(12) United States Patent
Yarborough et al.

(10) Patent No.: US 6,722,054 B2
(45) Date of Patent: Apr. 20, 2004

(54) PROCESS AND DELIVERY CONTAINER FOR LYOPHILIZING ACTIVE AGENT

(75) Inventors: Cody L. Yarborough, Fort Collins, CO (US); Dominic Gregory Madril, Loveland, CO (US); Rajan Bawa, Fort Collins, CO (US)

(73) Assignee: Atrix Laboratories, Inc., Fort Collins, CO (US)

( * ) Notice: Subject to any disclaimer, the term of this patent is extended or adjusted under 35 U.S.C. 154(b) by 0 days.

(21) Appl. No.: 09/909,671

(22) Filed: Jul. 20, 2001

(65) Prior Publication Data

US 2001/0042317 A1 Nov. 22, 2001

Related U.S. Application Data

(62) Division of application No. 09/190,341, filed on Nov. 12, 1998.

(51) Int. Cl.[7] ................................................. F26B 5/06
(52) U.S. Cl. ............................. 34/284; 34/285; 34/286; 34/69; 34/92; 34/287
(58) Field of Search ...................... 34/259, 266, 275, 34/278, 296, 284, 285, 286, 287, 288, 289, 69, 92; 422/100

(56) References Cited

U.S. PATENT DOCUMENTS

| | | | |
|---|---|---|---|
| 3,454,178 A | 7/1969 | Bender et al. | 215/37 |
| 4,172,457 A | 10/1979 | Choksi et al. | 128/272.1 |
| 4,250,139 A | 2/1981 | Luck et al. | 422/21 |
| 4,286,389 A | 9/1981 | Ogle | 34/5 |
| 4,521,975 A | * 6/1985 | Bailey | 34/5 |
| 4,729,208 A | 3/1988 | Galy et al. | 53/432 |
| 4,758,230 A | * 7/1988 | Rycroft | 604/118 |
| 4,829,006 A | 5/1989 | Smith et al. | 435/301 |
| 4,872,572 A | 10/1989 | Schrooten | 215/307 |
| 5,000,737 A | 3/1991 | Free et al. | 604/110 |
| 5,002,538 A | * 3/1991 | Johnson | 604/240 |
| 5,005,721 A | 4/1991 | Jordan | 220/23.4 |
| 5,279,608 A | 1/1994 | Cherif Cheikh | 604/892.1 |
| 5,352,756 A | 10/1994 | Meldal | 525/50 |
| 5,519,984 A | * 5/1996 | Beussink et al. | 53/489 |
| 5,542,935 A | 8/1996 | Unger et al. | 604/190 |
| 5,595,760 A | 1/1997 | Cherif-Cheikh | 424/464 |
| 5,653,693 A | 8/1997 | Miwa et al. | 604/187 |
| 5,770,559 A | 6/1998 | Manning et al. | 514/2 |
| 5,803,284 A | 9/1998 | Grimard | 215/249 |
| 5,807,345 A | 9/1998 | Grabenkort | 604/199 |
| 5,819,964 A | 10/1998 | Grimard | 215/249 |
| 5,882,603 A | 3/1999 | Taggart | 422/104 |

(List continued on next page.)

Primary Examiner—Ira S. Lazarus
Assistant Examiner—K. B. Rinehart
(74) Attorney, Agent, or Firm—Schwegman, Lundberg, Woessner & Kluth, P.A.

(57) ABSTRACT

A process for lyophilizing a solution of an active agent in a delivery container is provided. Solution of active agent is deposited into a delivery container, the container is covered with a covering plate and placed inside a lyophilizing apparatus. Lyophilization is conducted to dryness by radiation, convection or both. Also provided is a device made by this process, an active agent-plastic administration device such as a syringe containing an active agent in the form of lyophilized cake, and an array of such administration devices.

25 Claims, 5 Drawing Sheets

U.S. PATENT DOCUMENTS

| | | | |
|---|---|---|---|
| 5,900,422 A | 5/1999 | Ali | 514/316 |
| 5,916,526 A | 6/1999 | Robbins | 422/102 |
| 5,957,314 A | 9/1999 | Nishida et al. | 215/249 |
| 5,958,714 A | 9/1999 | Gordon et al. | 435/7.92 |
| 6,027,694 A | 2/2000 | Boulton et al. | 422/102 |
| 6,083,761 A | 7/2000 | Kedar et al. | 436/178 |
| 6,096,562 A | 8/2000 | Bunn et al. | 436/518 |
| 6,136,273 A | 10/2000 | Seguin et al. | 422/99 |
| 6,164,044 A | 12/2000 | Porfano et al. | 53/471 |
| 6,189,292 B1 | 2/2001 | Odell et al. | 53/425 |
| 6,221,854 B1 | 4/2001 | Radomsky | 514/54 |
| 6,224,883 B1 | 5/2001 | Roskos et al. | 424/400 |
| 6,241,949 B1 | 6/2001 | Kane | 422/102 |
| 6,305,413 B1 * | 10/2001 | Fischer et al. | 137/493.8 |
| 6,340,589 B1 | 1/2002 | Turner et al. | 435/287.2 |
| 6,436,351 B1 | 8/2002 | Gubernator et al. | 422/102 |

* cited by examiner

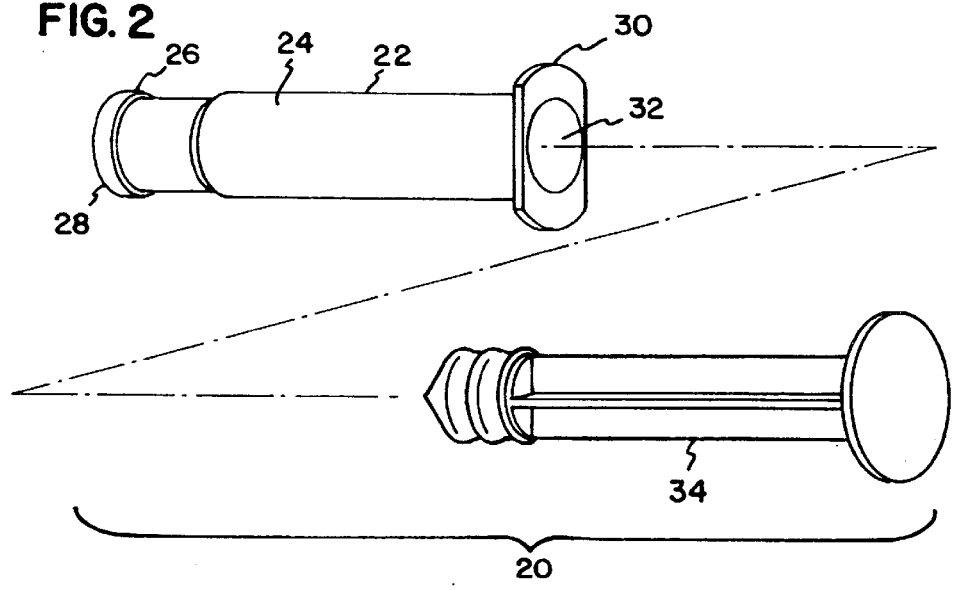
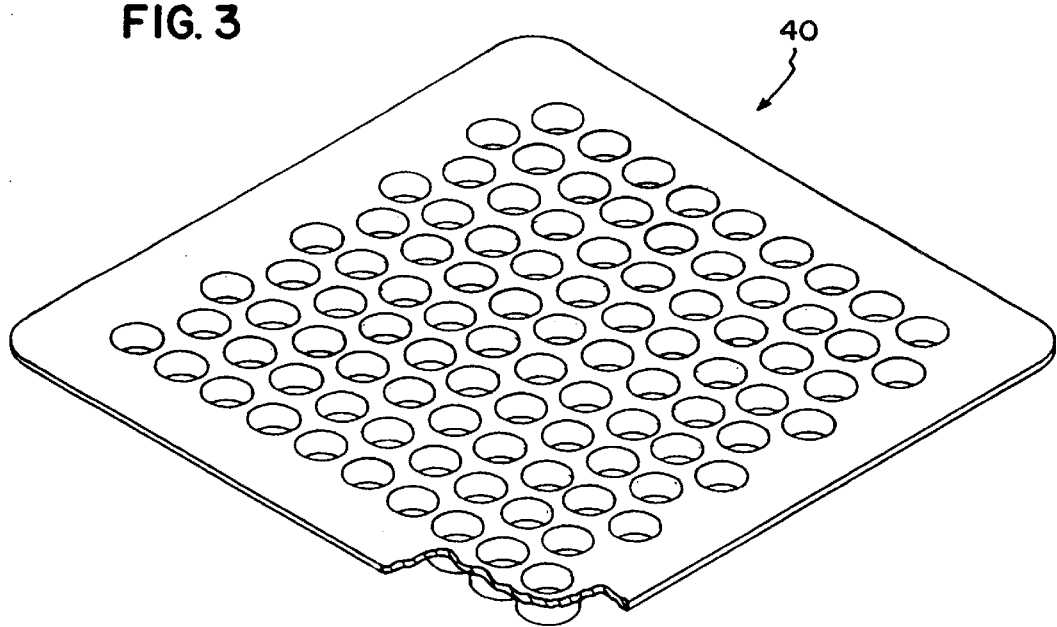

PROCESS AND DELIVERY CONTAINER FOR LYOPHILIZING ACTIVE AGENT

This application is a divisional of U.S. Ser. No. 09/190,341, filed on Nov. 12, 1998.

BACKGROUND OF THE INVENTION

1. Field of the Invention

The present invention relates to a process for lyophilizing a therapeutically-active agent in solution, and the delivery container for using the lyophilized active agent.

2. Description of the Prior Art

Lyophilization is a process which extracts liquid from a solution to form a granular solid or powder which is stable and easier to store at room temperature than the liquid. Lyophilization is carried out by freeze drying, or, more specifically, freezing followed by sublimation, which is the transition of a solid to the gaseous state without first passing through an intermediate liquid phase. Lyophilization is used instead of simply filling a container, such as a syringe, with a solid form of the active agent, because existing powder-filling equipment is incapable of filling to the precise tolerances required for some potent active agents, including various pharmaceuticals. The lyophilization process allows a larger quantity by weight of the active agent and suitable solvent to be filled in the container, thereby allowing for greater accuracy than powder-filling.

Lyophilization has many advantages compared to other drying and preserving techniques. It maintains the quality of the preserved substance, because the substance remains at a temperature that is below the freezing-point during sublimation. The resulting lyophilized matter can usually be stored without refrigeration, reducing storage and transportation costs of the substance as well as the storage space required for the product. It also reduces the weight of the lyophilized product, which similarly reduces shipping and related costs. In addition, lyophilized substances can be easily reconstituted prior to use, often in the very containers in which they were lyophilized and stored.

Lyophilization is particularly useful for preserving and storing various pharmaceuticals, because it increases their shelf-life. Moreover, the lyophilization can be performed in a syringe, and the lyophilized medication can be stored in the syringe. Diluent can then be added to the syringe for reconstitution of the medication, and the medication can be administered from the syringe to the patient.

Lyophilization has traditionally been performed in glass vials or ampules, but not syringes. Syringes, however, are the preferable means for lyophilization for active agents whose ultimate use will be from a syringe, since the active agent can be reconstituted and ultimately used in the syringe in which it was lyophilized. Lyophilization in a vial or ampule, on the other hand, requires transfer of the reconstituted active agent from the vial or ampule to the syringe. A particularly useful application for lyophilization in syringes would be for injectable pharmaceuticals.

Although lyophilization in syringes is known, as discussed and disclosed in U.S. Pat. Nos. 5,320,603, 5,184,450, 5,080,649, 4,874,381 and European Patent Application No. 0664137A2, there are problems and drawbacks with the known techniques. As discussed in U.S. Pat. No. 5,320,603, there are generally two types of syringes for lyophilization. A syringe for one-time use may be made containing lyophilized medication, to which diluent can be added to make the drug injectable. An example of such a syringe is disclosed in European Patent Application No. 0664137A2.

A second type of syringe contains two pistons, namely, a front or distal piston which separates the syringe barrel interior into two chambers, one containing the lyophilized medication and the other containing the diluent. This piston permits the bypass by axial displacement of diluent from one chamber to the other. The contents are mixed, and the second rear or proximal plunger-type piston is used to expel and dispense the reconstituted drug. Examples of this type of syringe are disclosed in U.S. Pat. Nos. 5,320,603 and 4,874,381.

As pointed out in U.S. Pat. No. 5,320,603, in both systems the syringe is prepared by filling the syringe barrel with a quantity of the medication in solvent to be lyophilized. The distal end of the syringe barrel is capped to maintain sterility. The proximal end contains a piston or plunger, which can allow the passage and escape of vapor during lyophilization. The syringe is lyophilized to drive off the vaporized solvent, which escapes through the distal end of the syringe barrel. The syringe is then ready for reconstitution with diluent prior to administration of the medication.

These disposable syringes are not readily susceptible to mass production, because they are costly to produce by the known methods. The known production methods generally require the use of many steps, special equipment, or both, as illustrated by U.S. Pat. No. 5,184,450. Regardless of the cost, current production is also difficult because of problems associated with capping the distal end of the syringe during lyophilization to preserve sterility.

In addition, although methods for lyophilization in plastic, as well as glass, syringes, is known, such as disclosed in European Patent Application No. 0664137A2A, there is no current commercial use of plastic syringes for lyophilization of medication. Glass syringes do not lend themselves as especially practical active agent delivery devices. The preferable means for administering injectable active agents, including pharmaceuticals, is by plastic syringe, which has many advantages over a glass syringe. Most notably, plastic syringes are cheaper, lighter, easier to use and safer than glass syringes.

One possible reason plastics are not being used for such commercial lyophilization is because plastics are less suitable for lyophilization containers than glass. Significantly, the thermal stresses associated with the cooling process of lyophilization limit the capability of some plastics to withstand the process, and these plastics tend to become brittle at temperatures at which glass remains intact. Consequently, lyophilization is rarely performed using plastic. It would be desirable to achieve lyophilization in plastic syringes if this problem could be overcome.

It is desired to make improvements to the known syringes and methods. It is desired to conduct lyophilization in mass produced, pre-sterilized, pre-packaged plastic syringes, which do not require any special plunger or any other unique syringe configuration to accommodate the lyophilization process. It is desired to use the same type of syringe for the lyophilization method of the present invention as is used for the administration of pharmaceuticals generally. In addition, by using a standard type of syringe, which is produced in an array of pre-sterilized and pre-packaged syringes on a plastic rack in a plastic tub, the entire tub can be put directly into a lyophilizing apparatus for lyophilization, thereby lending itself to mass production.

Moreover, whereas lyophilization is typically performed by conduction, it is desired to increase the ease and production efficiency of lyophilization by performing it by radiation, convection or both. It has not been shown that a container containing a substance to be lyophilized can be suspended within a lyophilizing apparatus, above and not in contact with any cooling surface of the lyophilizing apparatus. Lyophilization by such means would occur by radiation, convection or both. Lyophilization by radiation, convection, or both, would be easier than lyophilization by conduction, because lyophilization by the former methods is performed by simply loading a delivery container into a tub which is in turn placed into a lyophilizing apparatus. Lyophilization by conduction, however, requires manually placing the delivery container into the lyophilizing apparatus.

These and other advantages of the present invention will become apparent by referring to the detailed description of the preferred embodiment herein.

SUMMARY OF THE INVENTION

A process for lyophilizing a solution of an active agent is provided, by depositing the solution into a delivery container, covering the container with a covering plate, placing the container and covering plate inside a lyophilizing apparatus, and lyophilizing to dryness by radiation, convection or both.

A device made by this process is also provided.

Also provided is an active agent-plastic administration device, containing a single enclosed compartment, further containing an active agent in the form of lyophilized cake.

Also provided is an array of active agent-administration devices, containing an arrangement of administration devices, each having a single enclosed compartment, which compartment further contains an active agent in the form of lyophilized cake.

BRIEF DESCRIPTION OF THE DRAWINGS

FIG. 2 is a perspective view of a syringe as provided in accordance with the preferred embodiment of the present invention.

FIG. 3 is a perspective view of a rack used in the tub as provided in accordance with the preferred embodiment of the present invention.

DETAILED DESCRIPTION OF THE PREFERRED EMBODIMENT

Figure 1:
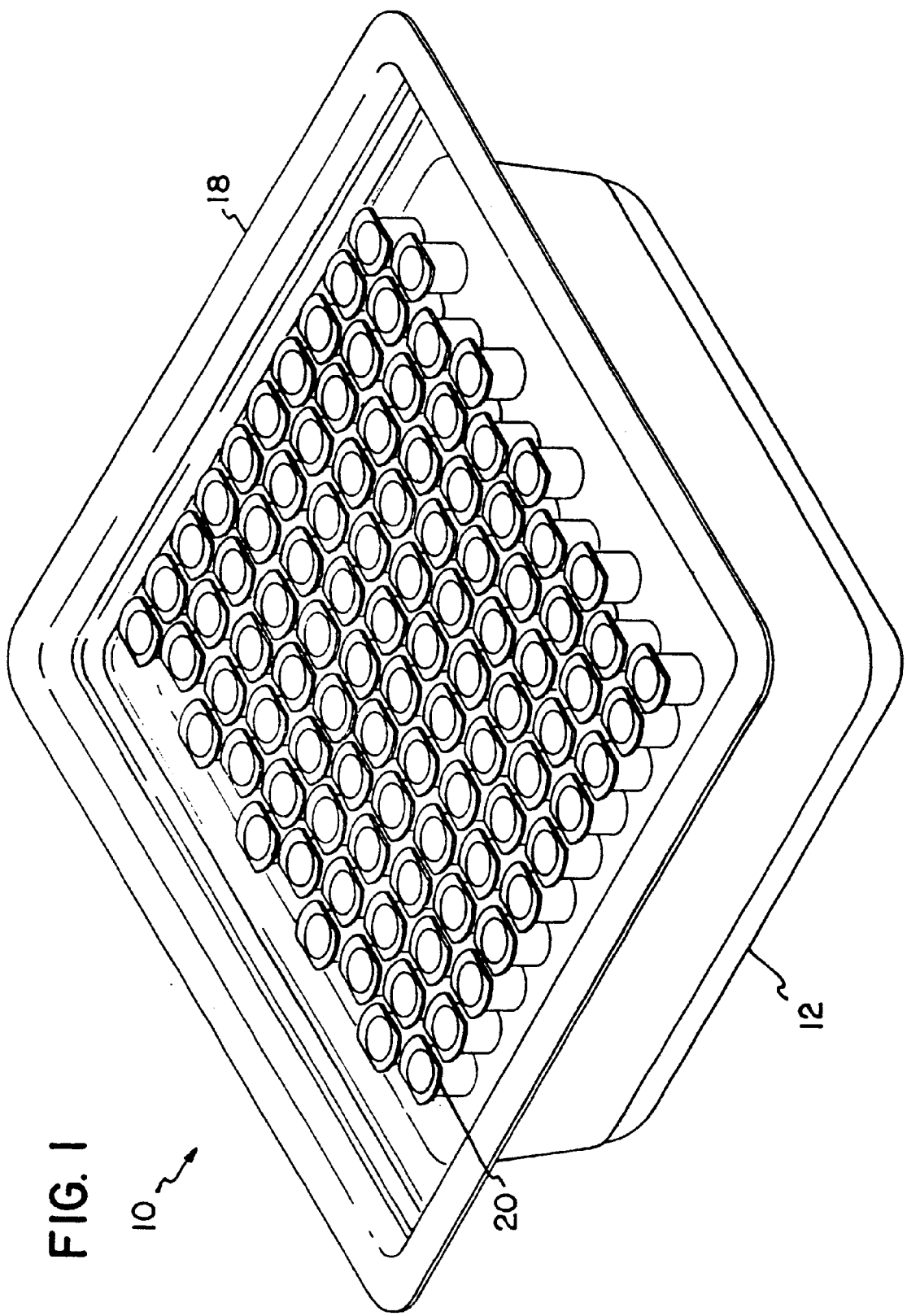
FIG. 1 is a perspective view of a tub, containing syringes on a rack, as provided in accordance with the preferred embodiment of the present invention.

The present invention relates to a process for lyophilizing a solution of an active agent, and a delivery container for using the active agent.

A pre-determined amount of active agent is mixed with a solvent suitable for lyophilizing a therapeutically-active agent to form a solution of active agent. "Active agent" is any therapeutically-active agent, and possible excipient, which can be lyophilized. "Excipient" includes any substance conventionally added to a therapeutically-active agent for ultimate constitution, examples of which are cryoprotectants, surfactants and bulking agents. While "solution" includes active agent that is entirely dissolved in solvent, it also includes active agent not so completely dissolved.

The solution is deposited into a delivery container. "Delivery container" is any receptacle in which the active agent can be lyophilized, reconstituted and ultimately used. An exemplary delivery container is a syringe.

The delivery container is loaded vertically into a plastic rack in a plastic tub, so the solution faces the bottom of the tub and the open end of the delivery container faces upward. In the case of a syringe, the syringe is loaded into the plastic rack in the tub, so a distal end of the syringe, covered by a cap, faces the bottom of the tub and a proximal end of the syringe, into which a plunger fits, faces upward. When more than one delivery container containing solution of active agent is being lyophilized concurrently, the multiple delivery containers are loaded into the plastic rack in the plastic tub.

It should be appreciated that, while the delivery container may be filled with solution before being placed into the tub, it may alternatively be placed in the tub first. That is, the delivery container may be loaded into the plastic rack in the plastic tub and then filled with solution. It should also be understood that multiple delivery containers may be lyophilized simultaneously, and that if more than one delivery container is being lyophilized concurrently, the multiple delivery containers may be loaded into the tub and then filled with solution.

After being loaded into the plastic tub, the delivery container is covered with a covering plate, which fits on a ledge extending around the periphery of the opening of the plastic tub. The "covering plate" is a lid of substantially planar shape used to cover the opening of the delivery container after the solution is deposited therein. It is used to allow the escape of vapor from the delivery container during lyophilization, while simultaneously preventing escape of the lyophilizate. "Lyophilizate" is the solid, powder or granular material resulting after lyophilization and the vacuum process.

The covering plate preferably includes a circular flange which fits around the opening of the delivery container, fitting so as to allow the passage of vapor from the delivery container but securely enough to prevent the escape of lyophilizate during lyophilization. The covering plate may include an array of such flanges, so as to be used during the lyophilization of multiple delivery containers simultaneously. The covering plate essentially forms a cap over the opening of each delivery container. It should be understood that the covering plate may fit on a ledge on the inside of the periphery of the plastic tub into which the delivery container is loaded, as long as the covering plate caps the delivery container, as described.

During lyophilization, any lyophilizate which contacts the covering plate is retained thereon. Lyophilization is performed to isolate a relatively small amount of active agent for its ultimate application, and thus, if any amount of active agent leaves a delivery container and is captured on the covering plate covering the delivery container, the amount of lyophilized active agent remaining in the delivery container is unknown. Thus, any delivery container losing any lyophilizate captured by the covering plate must be discarded.

Figure 4:
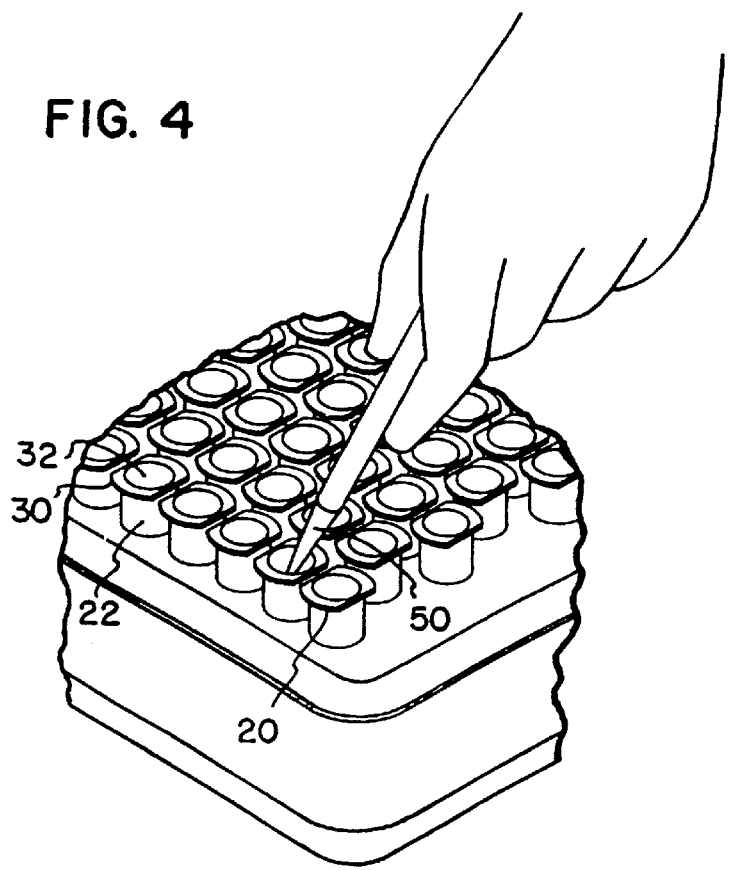
FIG. 4 is a perspective view of liquid medication being put into syringes on a rack in a tub, as provided in accordance with the preferred embodiment of the present invention.
Figure 5:
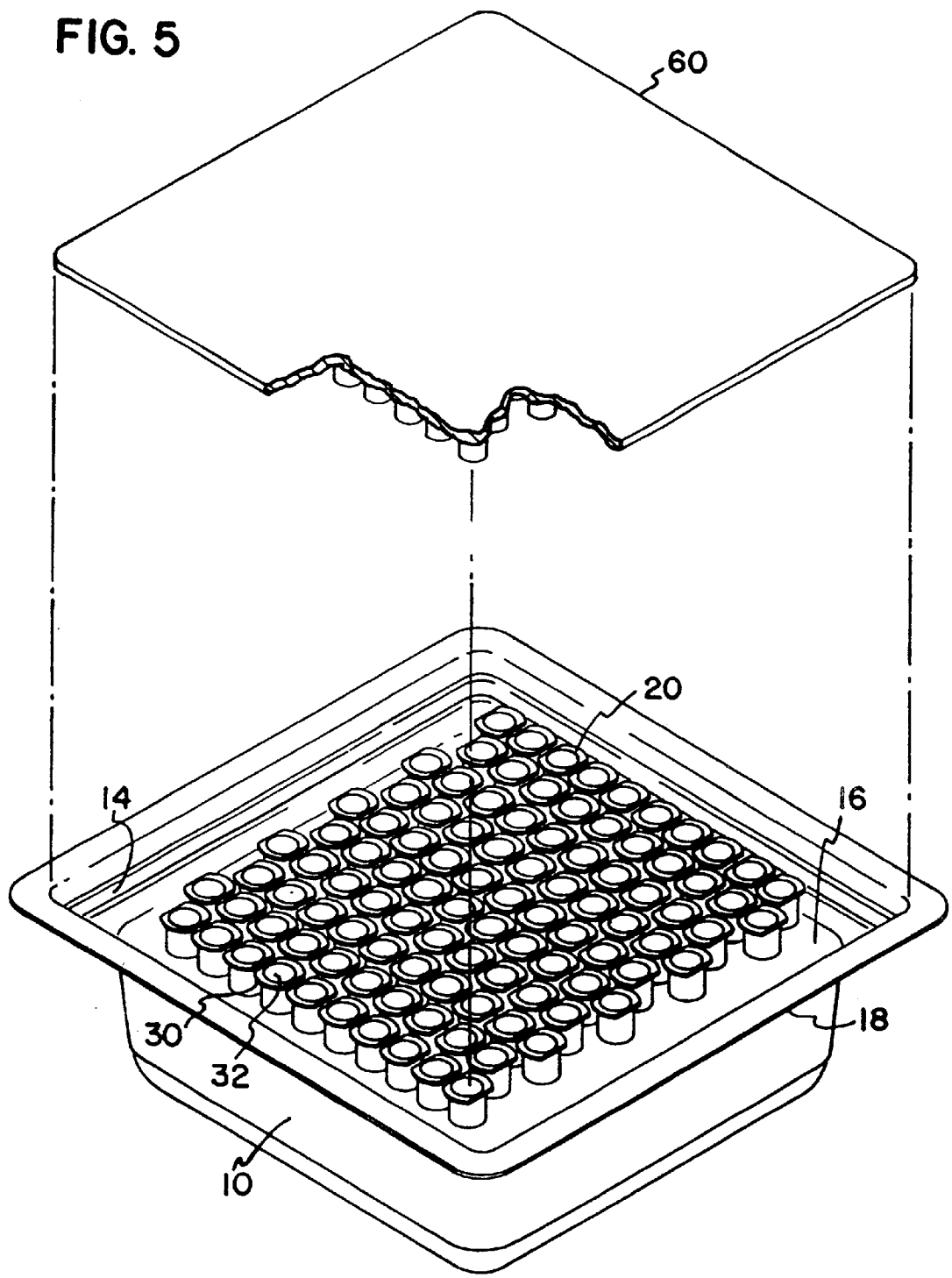
FIG. 5 is a perspective view of a covering plate being placed on a tub as provided in accordance with the preferred embodiment of the present invention.
Figure 6:
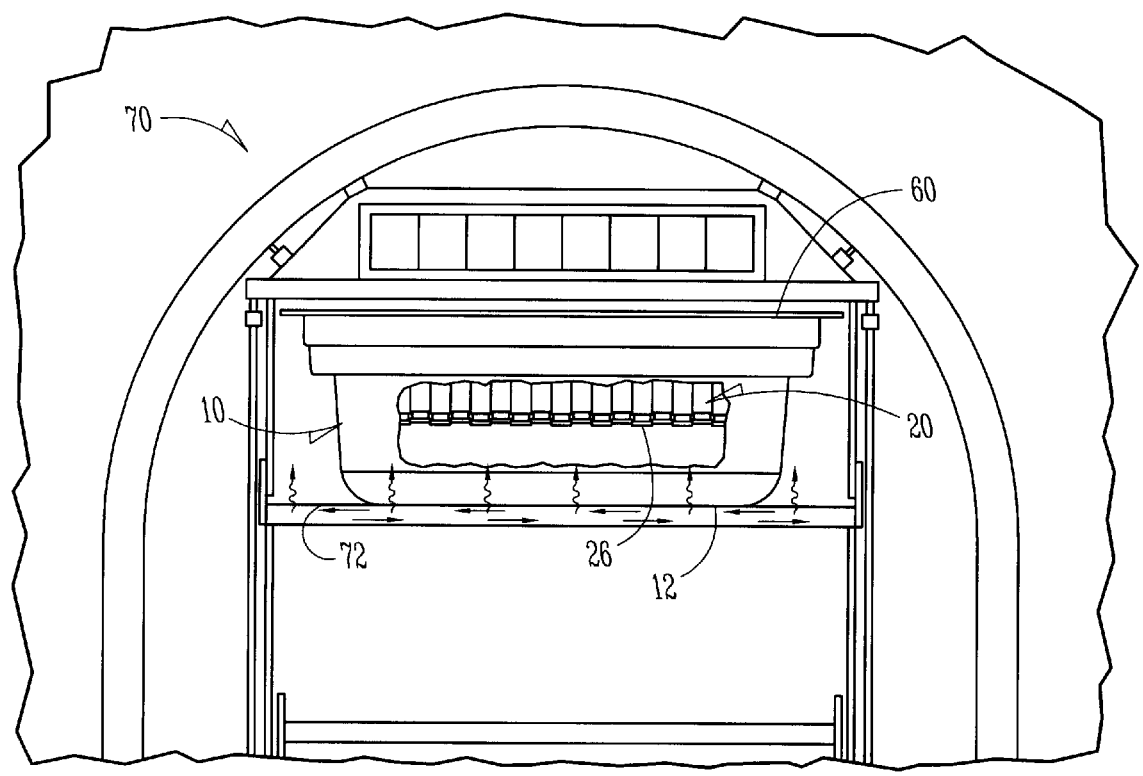
FIG. 6 is a frontal, partial cut-away view of a tub placed in a lyophilizing apparatus, as provided in accordance with the preferred embodiment of the present invention.

In addition to identifying any delivery container which loses lyophilized active agent captured by the covering plate during lyophilization, the covering plate prevents contamination of lyophilizate of one delivery container by the lyophilizate from another when multiple delivery containers are lyophilized simultaneously in close proximity.

The plastic tub, containing the filled delivery container, is placed into a lyophilizing apparatus, so that the bottom of the tub rests on the cooling shelf of the lyophilizing apparatus. The plastic rack inside the plastic tub suspends the delivery container above the surface of the bottom of the tub and prevents the delivery container from coming into contact with any cooling surface of the lyophilizing apparatus, such as a cooling shelf.

The cooling of the lyophilization is performed by radiation, convection or both, so that the solution is transformed into a frozen solid. Whereas lyophilization has traditionally been performed by conduction, lyophilization by convection, radiation, or both, is advantageous because these techniques increase economies of lyophilizing multiple delivery containers at the same time. Lyophilization by conduction occurs by placing the container containing the medication in intimate physical contact with the cooling surface of the lyophilizing apparatus, allowing cooling to occur by heat transfer as a result of the physical contact. Lyophilization is conventionally achieved by conduction because conduction is an effective means of heat transfer.

The present invention uses lyophilization by convection, radiation, or both, to increase the ease with which a number of delivery containers may be cooled simultaneously during lyophilization. Cooling by convection occurs by cooling of air being circulated around the matter being cooled. Cooling by radiation occurs by the emission of radiant energy in the form of waves or particles. Neither cooling by convection nor by radiation occurs by the physical contact of the delivery container with a cooling surface of the lyophilizing apparatus, and thus, cooling by these means occurs without such contact. In the present invention, lyophilization by convection, radiation, or both, is performed by suspending the delivery container to be lyophilized above the cooling surface of a lyophilizing apparatus. Specifically, the delivery container is suspended by the plastic rack within the plastic tub placed within the lyophilizing apparatus.

The cooling step makes the process of the present invention easier to perform and generally more user-friendly than lyophilization cooling by conduction. Whereas lyophilization by conduction requires manually placing each delivery container on to the cooling shelf of the lyophilizing apparatus, lyophilization in the present invention is performed by simply loading each delivery container into the tub which is in turn placed into the lyophilizing apparatus, allowing multiple delivery containers to be lyophilized with one simple step. This greatly increases the economies of lyophilization by the present invention over that of lyophilization by conduction.

Cooling by convection, radiation or both may take longer than cooling by conduction, and accordingly, the cooling of the present invention may take longer than cooling by conduction. However, the cooling time of the present invention is not prohibitively long, and the efficiencies realized by the present invention outweigh the increased cooling time.

After the solution is cooled to a frozen solid, a vacuum is applied to the lyophilizing apparatus to provide at least a partial vacuum within the delivery container and outside of the delivery container but still within the lyophilizing apparatus. The vacuum is applied to the solution to dryness. What is meant by "dryness" is that the liquid leaves the frozen solid to form the lyophilizate under conditions commonly known for the vacuum process. The cooling and vacuum processes are performed to remove liquid from the active agent in solution at low temperature by sublimation. This process is used as opposed to other methods so as not to denature, degrade or otherwise damage the active agent by heat.

After sublimation occurs to dryness, the tub is removed from the lyophilization apparatus. The covering plate is removed from on top of the delivery container and examined for any retained lyophilizate. If the covering plate contains any such lyophilizate, each delivery container from which the lyophilizate came is discarded. The solid, powder or granular material remaining in the delivery container after lyophilization is referred to as "lyophilizate cake." This is the undisturbed and intact usable active agent material resulting from lyophilization.

After lyophilization, the opening of any undiscarded delivery container is sealed for storage and prior to usage. The delivery container may be sealed with those apparatuses known for sealing delivery containers. Where the delivery container is a syringe, the opening of the syringe barrel is sealed with the plunger of the syringe.

When ready for use, the seal is removed from the delivery container and diluent is added to the delivery container for reconstitution. The lyophilized active agent is then ready to be used. Where the delivery container is a syringe, a cap covering a distal end of the syringe barrel is removed and a hypodermic needle is inserted to the distal end by screwing it on to threads which can receive the needle. The needle end of the syringe is then inserted into the receptacle containing the diluent, and the syringe plunger is withdrawn towards the proximal end of the syringe barrel until the appropriate amount of diluent is extracted into the syringe for reconstitution. The syringe is withdrawn from the diluent-containing receptacle, and the contents of the syringe are mixed by agitation until the lyophilized cake is dissolved or suspended in the diluent. The reconstituted active agent is now ready for administration.

Preferred Embodiment

A preferred embodiment of the process of the present invention is the lyophilization of an injectable pharmaceutical in a plastic syringe, or, more preferably, an array of plastic syringes. An example of such an array of syringes includes an array of pre-packaged, pre-sterilized, plastic syringes manufactured by Becton Dickinson and Company in what is known as a "Hypak" configuration and disclosed in U.S. Pat. No. 4,758,230.

In the present embodiment, the syringes are received pre-packaged and pre-sterilized in a tub 10, as shown in FIG. 1. Referring now to FIG. 2., each syringe 20 contains a barrel 22, within which is a chamber 24 for retaining fluid. A distal end 26 of the syringe barrel 22 is capped with a syringe cap 28. A proximal end 30 of the barrel contains an opening 32 which may accept a plunger 35, including a plunger tip 34 and plunger rod 33. The plunger tip 34 can be moved within the barrel 22 when the plunger rod 33 is pulled toward the proximal end 30 or pushed towards the distal end 26 of the barrel 22. The plunger tip 34 and plunger 35 generally can also be removed from the syringe barrel 22.

The syringes 20 are arranged in a plastic rack 40 in the tub 10, such that the distal ends 26 of the syringes face the bottom 12 of the tub 10 and the proximal ends 30 of the syringes 20 face upward. The plastic rack is shown in FIG. 3. By being in the rack 40, the syringes 20 are suspended above the bottom 12 of the tub 10.

Referring now to FIG. 4, the syringes 20 are filled with pharmaceutical in solution 50 from the openings 32 in the proximal ends 30 of the syringe barrels 22. As shown if FIG. 5, a covering plate 60 is then placed on a ledge 14 extending around the inside 16 of the periphery of the top 18 of the tub 10 and covering the openings 32 of the proximal ends 30 of the syringes 20. The tub 10 is placed on a shelf 72 inside the lyophilizing apparatus 70. The tub 10 as placed in the lyophilizing apparatus 70 is shown in FIG. 6.

The lyophilization apparatus 70 is then closed, and the pharmaceutical in solution 50 is cooled by radiation, convection or both, until the solution 50 is transformed into a frozen solid. After cooling, a vacuum is applied to the inside of the lyophilizing apparatus 70, including both inside the syringes 20 and outside the syringes 20, but still inside the lyophilizing apparatus 70. The vacuum is applied to dryness.

After lyophilization, the tub 10 of syringes 20 is removed from the lyophilizing apparatus 70. The covering plate 60 is removed from the proximal ends 30 of the syringes 20 and examined for any retained lyophilizate. If any area of the covering plate 60 contains retained lyophilizate, the syringe 20 from which the lyophilizate came is discarded.

A plunger tip 34 is inserted into the proximal end 30 of each syringe barrel 22 of each remaining syringe 20. With the use of the Becton Dickinson and Company "Hypak" configuration of pre-packaged syringes, after the covering plate 60 is removed following lyophilization, the plunger tips 34 may be inserted into the barrels 22 of the corresponding syringes 20 with one step. The "Hypak" arrangement provides plunger tips 34 connected to a two-dimensional grid or array, which allows the plunger tips 34 to be removed from or replaced into the barrels 22 of the corresponding syringes 20 with a single step. The plunger rods 33 are thereafter screwed into corresponding plunger tips 34. This further increases the efficiency with which lyophilization according to this embodiment occurs.

Figure 7:
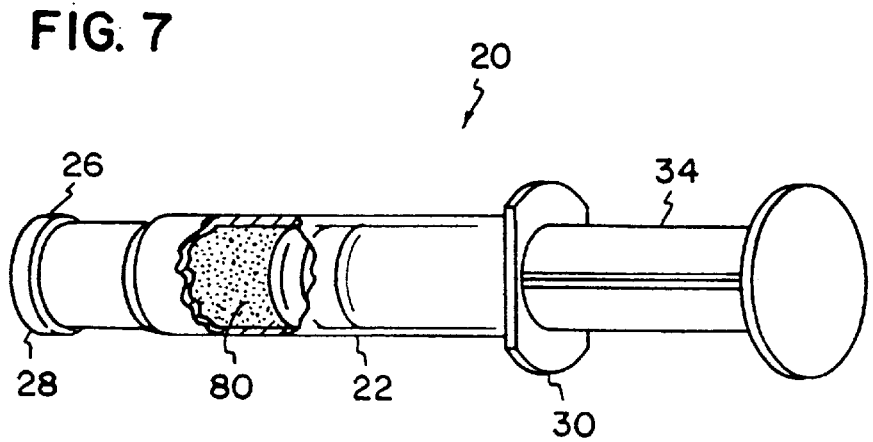
FIG. 7 is a perspective view of a syringe containing lyophilized medication as provided in accordance with the preferred embodiment of the present invention.

The syringes 20 are ready for subsequent storage and use. A syringe 20 containing lyophilized medication 80 is shown in FIG. 7. When ready for use, the cap 28 is removed from the distal end 26 of the syringe barrel 22, and diluent is added to the syringe 20 through the distal end 26 of the barrel 22. Reconstitution of the lyophilized medication 80 occurs by instantaneous dissolution, agitation, or passing the lyophilizate/diluent mixture between two syringes until a homogenous suspension is achieved. The dissolved or suspended contents are administered from the syringe 20 to a patient through a needle, cannula or other delivery mechanism.

An example of the use of this preferred embodiment is the lyophilization of leuprolide acetate by the process of this embodiment. A solution containing approximately 38 mg/ml of leuprolide acetate in water is prepared by mixing the leuprolide acetate in water until dissolved. A tub of syringes described in this embodiment is opened so the proximal openings of the syringes are exposed. Approximately 0.3 milliliters of the leuprolide acetate solution is filled into the syringes by means of a pipette through the proximal opening of each syringe. When all the syringes are filled with the drug solution, the tub containing the syringes is placed on the shelf of the lyophilizing apparatus. The lyophilizing apparatus shelf has a refrigerant circulating within the shelf to control temperature. The temperature of the shelf is reduced to approximately −50° C. until the solution in the syringes is frozen well below 0° C. by radiant and/or convectant cooling. Vacuum is applied to the chamber and the shelf temperature is slowly raised to room temperature until the water in the syringes is removed by sublimation. The result is a lyophilized powder in the syringes of approximately 11.4 milligrams.

The tub is removed from the lyophilizing apparatus. Plunger tips are installed into the proximal openings of the syringes, and plunger rods are screwed into the corresponding plunger tips. The syringes are now ready for reconstitution.

Active Agent

Active agent includes any therapeutically-active agent, and possible excipient, which can be lyophilized. Excipients tend to increase the stability and the ease of suspension and reconstitution of therapeutically-active agents for and during lyophilization. An exemplary category of excipient includes ionic and non-ionic (amphoteric) surfactants, specific examples of which include polysorbates, cremophores and tyloxopols. Another type of exemplary excipient includes bulking agents, specific examples of which include sodium and potassium phosphates, citric acid, tartaric acid, gelatins, and carbohydrates such as dextrose, mannitol and dextran. An additional type of exemplary excipient is lyoprotectants, including glucose, catalase, maltose, maltotriose and maltohexose.

Examples of suitable therapeutically-active agents include substances capable of prevention an infection systemically in an animal or human, or locally at the defect site, for example, antibacterial agents such as penicillin, cephalosporins, bacitracin, tetracycline, doxycycline, gentamycin, quinolines, neomycin, clindamycin, kanamycin, and metronidazole; anti-inflammatory agents such as hydrocortisone, and prednisone; antiparasitic agent such as quinacrine, chloroquine, and vidarbine; antifungal agents such as nystatin; antiviral agents such as acyclovir, ribarivin, and interferons; analgesic agents such as salicylic acid, acetaminophen, ibuprofen, naproxen, piroxicam, flurbiprofen, and morphine; local anesthetics such as cocaine, lidocaine, bupivacaine and benzocaine; immunogens (vaccines) for simulating antibodies against hepatitis, influenza, measles, rubella, tetanus, polio, and rabies; peptides such as leuprolide acetate (an LH-RH agonist), nafarelin, ganirelix, and goserelin.

Substances, or metabolic precursors thereof, which are capable of promoting growth and survival of cells and tissues or augmenting the functioning of cells can also be used, for example, a nerve growth promoting substance, such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-α), transforming growth factor-β (TGF-β), epidermal growth factor (EGF), fibroblast growth factor (FGF), interleukin-1 (IL-1), and prostaglandins such as $PGE_1$, $PGE_2$ and $PGD_2$; an osteoinductive agent or bone growth promoting substance such a bone chips or demineralized bone material; and antineoplastic agents such as methotrexate, 5-fluouracil, adriamycin, vinblastine, cisplatin, tumor-specific antibodies conjugated to toxins, and tumor necrosis factor.

Other suitable active agents include hormones such as progesterone, testosterone, follicle simulating hormone (FSH) (used for birth control and fertility-enhancement), insulin, and somatotropins; antihistamines such as diphenhydramine and chlorphencramine; cardiovascular agents such as digitalis, nitroglycerine, papaverine and streptokinase; anti-ulcer agents such as cimetidine hydrochloride, and isopropamide iodide; bronchodilators such as metaproternal sulfate and aminophylline; vasodilators such as theophylline, niacin and minoxidil; central nervous system agents such as tranquilizer, b-adrenergic blocking agents, and dopamine; antipsychotic agents such as risperidone and olanzapine; narcotic antagonists such as naltrexone, naloxone and buprenorphine.

Additional examples of suitable active agents are provided in U.S. Pat. No. 5,234,529, the disclosure of which is incorporated by reference herein.

Delivery Container

The delivery container includes any receptacle in which an active agent can be lyophilized, reconstituted and ultimately used.

An exemplary and preferable delivery container is a syringe. Although the use of glass vials or ampules for lyophilization is quite common, the use of syringes for lyophilization is uncommon. Syringes, however, are the preferable means for lyophilization for active agents whose ultimate use will be from a syringe, since the active agent can be used for its ultimate application after reconstitution in the syringe in which it was lyophilized. Lyophilization in a vial or ampule, on the other hand, requires transfer of the reconstituted active agent from the vial or ampule to the syringe. Syringes would be especially useful for lyophilizing injectable medications, since the medications are ultimately administered in the syringes.

Plastic syringes, as opposed to glass syringes, are the preferable delivery container, since plastic syringes are the drug delivery vehicle of choice for injectable medications. Glass syringes are susceptible to breakage and are more fragile than plastic syringes. Alternatively, plastic syringes are stronger, and thus, safer for health care professionals to use both in reconstituting and administering injectable medications. Plastic syringes are also lighter and cheaper than glass syringes.

In addition, the bore size of commercially-available glass syringes typically is quite small, requiring a greater amount of force to use the syringe than with a larger bore size. Because plastic is stronger than glass, the bore size of plastic syringes can be made larger than those of comparable glass syringes, decreasing the force required to use the syringe.

This is especially useful when reconstituting an injectable medication with a very viscous diluent, particularly for syringe-to-syringe to reconstitution. For syringe-to-syringe reconstitution, two syringes are used, the distal end of the second syringe (male syringe) being able to be securely screwed and fit into the distal end of the first syringe (female syringe). The first syringe contains diluent. The second syringe contains lyophilized medication. The tip caps covering the distal ends of each syringe are removed, and the two syringes are coupled securely together. The diluent of the first syringe is injected into the second syringe by pushing the plunger of the first syringe toward the distal end of that syringe, allowing the diluent to be mixed with the lyophilized medication. The mixed contents are then pushed back into the first syringe, by pushing the plunger of the second syringe toward the distal end of that syringe. This entire operation is a mixing cycle. Most syringe-to-syringe reconstitution requires dozens of mixing cycles.

Because plastic for syringes is generally lighter, cheaper and stronger than glass, plastic syringes are also cheaper to manufacture than glass syringes, further adding to the advantages of the present invention.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method for lyophilizing a solution comprising an active agent, the method comprising in any order: (a) applying a vacuum to the solution and (b) cooling the solution, for a period of time effective to provide lyophilizate;

wherein, the solution comprising the active agent is located in a plastic syringe having an open end;

the plastic syringe is located in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate from the plastic syringe;

such that the rack suspends he plastic syringe above any surface of the tub and prevents the plastic syringe from coming into contact with the cooling source of the lyophilizing apparatus.

2. The method of claim 1 wherein the active agent is leuprolide acetate.

3. The method of claim 1 wherein about 0.3 ml of the solution comprising the active agent is located in the plastic syringe.

4. The method of claim 1 wherein the solution comprises about 38 mg/ml of leuprolide acetate.

5. The method of claim 1 wherein about 11.4 mg of lyophilizate is obtained from the lyophilization.

6. The method of claim 1 wherein the solution is cooled to a temperature between about 0° C. and −50° C.

7. The method of claim 1 wherein the plastic syringe is pre-sterilized, pre-packaged, or a combination thereof.

8. The method of claim 1 wherein the plastic syringe is a female syringe of a syringe-to-syringe assembly.

9. The method of claim 1 wherein the plastic syringe is a male syringe of a syringe-to-syringe assembly.

10. The method of claim 1 wherein the covering plate comprises a circular flange which fits around the opening of the plastic syringe.

11. The method of claim 1 wherein more than one syringe is employed.

12. The method of claim 11 wherein the covering plate comprises an array of circular flanges.

13. The method of claim 1 wherein the cooling source of the lyophilizing apparatus cools the solution by radiation.

14. The method of claim 1 wherein the cooling source of the lyophilizing apparatus cools the solution by convection.

15. The method of claim 1 wherein the cooling source of the lyophilizing apparatus cools the solution by convection and radiation.

16. A method for lyophilizing a solution comprising leuprolide acetate, the method comprising in any order: (a) cooling the solution, for a period of time effective and (b) applying a vacuum to the solution for a period of time effective to provide a lyophilizate of leuprolide acetate;

wherein, the solution comprising the leuprolide acetate is located in a plastic syringe having an open end;

the plastic syringe is located in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate of leuprodide acetate from the plastic syringe;

such that the rack suspends the plastic syringe above any surface of the tub and prevents the plastic syringe from coming into contact with the cooling source of the lyophilizing apparatus.

17. A method for lyophilizing a solution comprising an active agent, the method comprising in any order: (a) cooling the solution, for a period of time effective and (b) applying a vacuum to the solution for a period of time effective to provide a lyophilizate of leuprolide acetate; wherein, about 0.3 ml of the solution comprising the active agent is located in the plastic syringe having an open end;

the plastic syringe is locate in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate from the plastic syringe;

such that the rack suspends the plastic syringe above any surface of the tub and prevents the plastic syringe from coming into contact with the cooling source of the lyophilizing apparatus.

18. A method for lyophilizing a solution comprising an active agent, the method comprising in any order: (a) cooling the solution, for a period of time effective and (b) applying a vacuum to the solution for a period of time effective to provide a lyophilizate of leuprolide acetate; wherein, the solution comprising the active agent comprises about 38 mg/ml of leuprolide acetate and is located in a plastic syringe having an open end;

the plastic syringe is locate in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate from the plastic syringe;

such that the rack suspends he plastic syringe above any surface of the tub and prevents the plastic syringe from coming into contact with the cooling source of the lyophilizing apparatus.

19. A method for lyophilizing a solution comprising an active agent, the method comprising in any order: (a) cooling the solution, for a period of time and (b) applying a vacuum to the solution for a period of time effective to provide about 11.4 mg of lyophilizate obtained from the lyophilization;

wherein, the solution comprising the active agent is located in a plastic syringe having an open end;

the plastic syringe is locate in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate from the plastic syringe;

such that the rack suspends the plastic syringe above any surface of the tub and prevents the plastic syringe from coming into contact with the cooling source of the lyophilizing apparatus.

20. A method for lyophilizing a solution comprising an active agent, the method comprising in any order: (a) cooling the solution, for a period of time and (b) applying a vacuum to the solution for a period of time effective to provide a lyophilizate;

wherein, the solution comprising the active agent is located in a plastic male syringe of a syringe-to-syringe assembly having an open end;

the plastic syringe is locate in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate from the plastic syringe;

such that the rack suspends he plastic syringe above any surface of the tub and prevents the plastic syringe from coming into contact with the cooling source of the lyophilizing apparatus.

21. A method for lyophilizing a solution comprising an active agent, the method comprising in any order: (a) cooling the solution, for a period of time and (b) applying a vacuum to the solution for a period of time effective to provide a lyophilizate;

wherein, the solution comprising the active agent is located in a plastic syringe having an open end;

the plastic syringe is locate in a rack;

the rack is located in a tub;

the tub is located in a lyophilizing apparatus, wherein the lyophilizing apparatus comprises a cooling source; and a covering plate is removably attached to the open end of the plastic syringe, such that the covering plate allows vapor from the plastic syringe to pass during lyophilization and prevents the escape of lyophilizate from the plastic syringe and wherein the covering plate comprises a circular flange which fits around t opening of the plastic syringe;

such that the rack suspends the plastic syringe above any surface of the tub and prevents the plastic syringe from coming into contact with the cooling source of the lyophilizing apparatus.

22. A method for lyophilizing a solution comprising an active agent, the method comprising in any order: (a) cooling the solution, for a period of time and (b) applying a vacuum to the solution for a period of time effective to provide a lyophilizate;
wherein,
the solution comprising the active agent is located in plastic syringes having open ends;
the plastic syringes are located in a rack;
the rack is located in a tub;
the tub is located in a lyophilizing apparatus, wherein the lyophilizing apparatus comprises a cooling source; and
a covering plate is removably attached to the open end of the plastic syringes, such that the covering plate allows vapor from the plastic syringes to pass during lyophilization and prevents the escape of lyophilizate from the plastic syringes, wherein the covering plate comprises an array of circular flanges;
such that the rack suspends the plastic syringes above any surface of the tub and prevents the plastic syringes from coming into contact with the cooling source of the lyophilizing apparatus.

23. A method for lyophilizing a solution comprising an active agent, the method comprising in any order: (a) cooling the solution, for a period of time and (b) applying a vacuum to the solution for a period of time effective to provide a lyophilizate;
wherein,
the solution comprising the active agent is located in a plastic syringe having an open end;
the plastic syringe is located in a rack;
the rack is located in a tub;
the tub is located in a lyophilizing apparatus, wherein the lyophilizing apparatus comprises a cooling source, wherein the cooling source of the lyophilizing apparatus cools the solution by radiation; and
a covering plate is removably attached to the open end of the plastic syringe, such that the covering plate allows vapor from the plastic syringe to pass during lyophilization and prevents the escape of lyophilizate from the plastic syringe;
such that the rack suspends the plastic syringe above any surface of the tub and prevents the plastic syringe from coming into contact with the cooling source of the lyophilizing apparatus.

24. A method for lyophilizing a solution comprising an active agent, the method comprising in any order: (a) cooling the solution, for a period of time and (b) applying a vacuum to the solution for a period of time effective to provide a lyophilizate;
wherein,
the solution comprising the active agent is located in a plastic syringe having an open end;
the plastic syringe is locate in a rack;
the rack is located in a tub;
the tub is located in a lyophilizing apparatus, wherein the lyophilizing apparatus comprises a cooling source, wherein the cooling source of the lyophilizing apparatus cools the solution by convection; and
a covering plate is removably attached to the open end of the plastic syringe, such that the covering plate allows vapor from the plastic syringe to pass during lyophilization and prevents the escape of lyophilizate from the plastic syringe;
such that the rack suspends the plastic syringe above any surface of the tub and prevents the plastic syringe from coming into contact with the cooling source of the lyophilizing apparatus.

25. A method for lyophilizing a solution comprising an active agent, the method comprising in any order: (a) cooling the solution, for a period of time and (b) applying a vacuum to the solution for a period of time effective to provide a lyophilizate;
wherein,
the solution comprising the active agent is located in a plastic syringe having an open end;
the plastic syringe is locate in a rack;
the rack is located in a tub;
the tub is located in a lyophilizing apparatus, wherein the lyophilizing apparatus comprises a cooling source, wherein the cooling source of the lyophilizing apparatus cools the solution by convection and radiation; and
a covering plate is removably attached to the open end of the plastic syringe, such that the covering plate allows vapor from the plastic syringe to pass during lyophilization and prevents the escape of lyophilizate from the plastic syringe;
such that the rack suspends the plastic syringe above any surface of the tub and prevents the plastic syringe from coming into contact with the cooling source of the lyophilizing apparatus.

* * * * *

UNITED STATES PATENT AND TRADEMARK OFFICE
CERTIFICATE OF CORRECTION

PATENT NO. : 6,722,054 B2
DATED : April 20, 2004
INVENTOR(S) : Yarborough et al.

It is certified that error appears in the above-identified patent and that said Letters Patent is hereby corrected as shown below:

Column 10,
Line 9, after "provide" insert -- a --.
Line 24, delete "he" and insert -- the --, therefor.

Column 11,
Line 8, delete "leuprodide" and insert -- leuprolide --, therefor.
Lines 21 and 45, delete "locate" and insert -- located --, therefor.
Line 55, delete "he" and insert -- the --, therefor.

Column 12,
Lines 1, 25 and 49, delete "locate" and insert -- located --, therefor.
Line 36, delete "he" and insert -- the --, therefor.
Line 59, delete "t" and insert -- the --, therefor.

Column 14,
Lines 6 and 31, delete "locate" and insert -- located -- , therefor.

Signed and Sealed this

Seventh Day of September, 2004

JON W. DUDAS
*Director of the United States Patent and Trademark Office*